United States Patent [19]

Burckhardt

[11] Patent Number: 4,732,908
[45] Date of Patent: Mar. 22, 1988

[54] METHOD AND COMPOSITIONS FOR CONTROLLING INSECTS, AND MEMBERS OF THE ORDER ACARINA, WHICH COMPOSITIONS CONTAIN, AS ACTIVE INGREDIENTS 2-(1-INDOLINYL-METHYL)-IMIDAZOLINES OR SALTS THEREOF

[75] Inventor: Urs Burckhardt, Basel, Switzerland

[73] Assignee: Ciba-Geigy Corporation, Ardsley, N.Y.

[21] Appl. No.: 23,931

[22] Filed: Mar. 9, 1987

Related U.S. Application Data

[63] Continuation of Ser. No. 635,695, Jul. 30, 1984, abandoned.

[30] Foreign Application Priority Data

Aug. 9, 1983 [CH] Switzerland .......... 4334/83
Jul. 11, 1984 [CH] Switzerland .......... 3362/84

[51] Int. Cl.[4] .......... A01N 43/50; C07D 403/06
[52] U.S. Cl. .......... 514/402; 548/348
[58] Field of Search .......... 548/348; 514/402

[56] References Cited

U.S. PATENT DOCUMENTS

| 2,909,523 | 10/1959 | Bach et al. .......... | 546/165 |
| 3,404,156 | 1/1968 | Archer .......... | 548/348 |
| 4,104,392 | 8/1978 | Okamoto et al. .......... | 546/165 |
| 4,442,111 | 4/1984 | Muller et al. .......... | 546/158 |

FOREIGN PATENT DOCUMENTS

| 1670143 | 12/1970 | Fed. Rep. of Germany ...... | 548/348 |
| 2937779 | 4/1981 | Fed. Rep. of Germany ...... | 546/165 |
| 1191963 | 5/1970 | United Kingdom ................ | 548/348 |

OTHER PUBLICATIONS

*Stedman's Medical Dictionary*, 23rd edit., (Williams & Wilkins, 1976), pp. 91 and 648.

*Primary Examiner*—Henry R. Jiles
*Assistant Examiner*—Kurt G. Briscoe
*Attorney, Agent, or Firm*—Edward McC. Roberts; Kevin T. Mansfield

[57] ABSTRACT

The use in pest control of 2-(1-indolinylmethyl)-imidazolines of the formula I

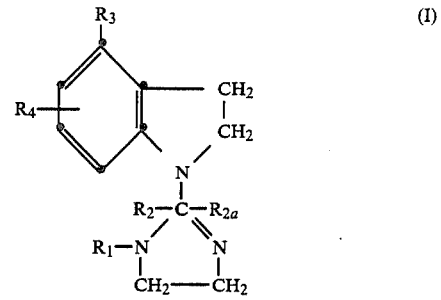

or salts thereof, wherein
$R_1$ is hydrogen or $C_1$–$C_{12}$-alkyl,
$R_2$ and $R_{2a}$ independently of one another are each hydrogen or $C_1$–$C_4$-alkyl, or together are $C_2$–$C_4$-alkylene, and
$R_3$ and $R_4$ independently of one another are each hydrogen, halogen or $C_1$–$C_3$-alkoxy, or $C_1$–$C_4$-alkyl which is unsubstituted or substituted by halogen.

There are also described the compounds of the formula Ia

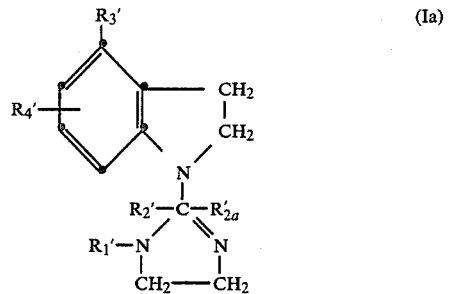

wherein
$R_1'$ is hydrogen or $C_1$–$C_{12}$-alkyl,
$R_2'$ and $R_{2a}'$ independently of one another are each hydrogen or $C_1$–$C_4$-alkyl, or together are $C_2$–$C_4$-alkylene,
$R_3'$ is hydrogen, halogen or $C_1$–$C_3$-alkoxy, or $C_1$–$C_4$-alkyl which is unsubstituted or substituted by halogen, and
$R_4'$ is halogen or $C_1$–$C_3$-alkoxy, or $C_1$–$C_4$-alkyl which is unsubstituted or substituted by halogen, or
$R_3'$ is halogen or $C_1$–$C_3$-alkoxy, or $C_1$–$C_4$-alkyl which is unsubstituted or substituted by halogen, and
$R_4'$ is hydrogen, halogen or $C_1$–$C_3$-alkoxy, or $C_1$–$C_4$-alkyl which is unsubstituted or substituted by halogen,
and processes for producing these compounds.

9 Claims, No Drawings

METHOD AND COMPOSITIONS FOR CONTROLLING INSECTS, AND MEMBERS OF THE ORDER ACARINA, WHICH COMPOSITIONS CONTAIN, AS ACTIVE INGREDIENTS 2-(1-INDOLINYL-METHYL)-IMIDAZOLINES OR SALTS THEREOF

This application is a continuation of application Ser. No. 635,695, filed July 30, 1984, now abandoned.

The present invention relates to compositions for controlling insects, and members of the order Acarina, which compositions contain, as active ingredients, 2-(1-indolinyl-methyl)-imidazolines or salts thereof, to the use of these 2-(1-indolinyl-methyl)-imidazolines, to the novel 2-(1-indolinyl-methyl)-imidazolines, and to a process for producing them.

The 2-(1-indolinylmethyl)-imidazolines correspond to the formula I

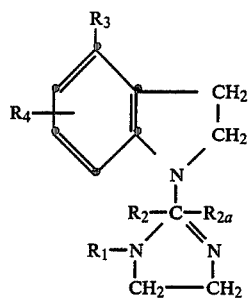 (I)

wherein $R_1$ is hydrogen or $C_1$–$C_{12}$-alkyl, $R_2$ and $R_{2a}$ independently of one another are each hydrogen or $C_1$–$C_4$-alkyl, or together are $C_2$–$C_4$-alkylene, and $R_3$ and $R_4$ independently of one another are each hydrogen, halogen or $C_1$–$C_3$-alkoxy, or $C_1$–$C_4$-alkyl which is unsubstituted or substituted by halogen, By halogen is meant in this case fluorine, chlorine, bromine or iodine, especially chlorine or fluorine.

The alkyl or alkoxy groups denoted by $R_1$ to $R_4$ can be straight-chain or branched-chain.

Examples of alkoxy groups, and of alkyl groups which are unsubstituted or substituted by halogen, in the case of $R_1$ to $R_4$ are, inter alia: methyl, methoxy, trifluoromethyl, ethyl, ethoxy, propyl, propoxy, isopropyl, n-, i-, sec- or tert-butyl, n-pentyl, n-hexyl, n-heptyl and n-dodecyl, and isomers thereof.

By $C_2$–$C_4$-alkylene are meant, inter alia, ethylene and butylene.

Suitable for salt formation are inorganic acids, for example: HCl, $H_2SO_4$, HBr or $H_3PO_4$; and organic acids, for example: saturated and unsaturated mono-, di- and tricarboxylic acids, such as formic acid, acetic acid, trifluoroacetic acid, oxalic acid, phthalic acid, succinic acid, benzoic acid, p-methylphenylsulfonic acid and citric acid.

In the German Offenlegungsschrift No. 1,670,143, the compound of the formula

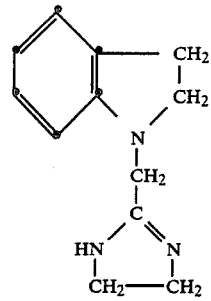

is described as "Vascoconstrictor".

Novel compounds are those of the formula

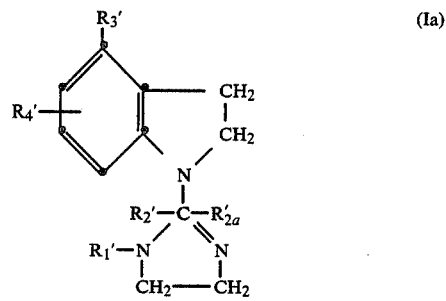 (Ia)

or salts thereof, wherein $R_1'$ is hydrogen or $C_1$–$C_{12}$-alkyl, $R_2'$ and $R_{2a}'$ independently of one another are each hydrogen or $C_1$–$C_4$-alkyl, or together are $C_2$–$C_4$-alkylene, $R_3'$ is hydrogen, halogen or $C_1$–$C_3$-alkoxy, or $C_1$–$C_4$-alkyl which is unsubstituted or substituted by halogen, and $R_4'$ is halogen or $C_1$–$C_3$-alkoxy, or $C_1$–$C_4$-alkyl which is unsubstituted or substituted by halogen, or $R_3'$ is halogen or $C_1$–$C_3$-alkoxy, or $C_1$–$C_4$-alkyl which is unsubstituted or substituted by halogen, and $R_4'$ is hydrogen, halogen or $C_1$–$C_3$-alkoxy, or $C_1$–$C_4$-alkyl which is unsubstituted or substituted by halogen.

Preferred compounds of the formula Ia are those wherein $R_1'$ and $R_{2a}'$ are hydrogen, $R_2'$ is hydrogen or $C_1$–$C_4$-alkyl, $R_3'$ is halogen or $C_1$–$C_3$-alkoxy, or $C_1$–$C_4$-alkyl which is unsubstituted or substituted by fluorine, and $R_4'$ is hydrogen, halogen or $C_1$–$C_4$-alkyl.

Particularly preferred compounds of the formula Ia are those wherein $R_1'$, $R_2'$, $R_{2a}'$ and $R_4'$ are hydrogen, and $R_3'$ is halogen or $C_1$–$C_3$-alkoxy, or $C_1$–$C_4$-alkyl which is unsubstituted or substituted by fluorine.

The compounds of the formula Ia, and the compound known from German Offenlegungsschrift No. 1,670,143 of the formula

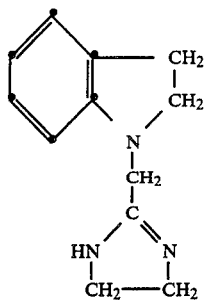

are produced by methods known per se, for example as follows:

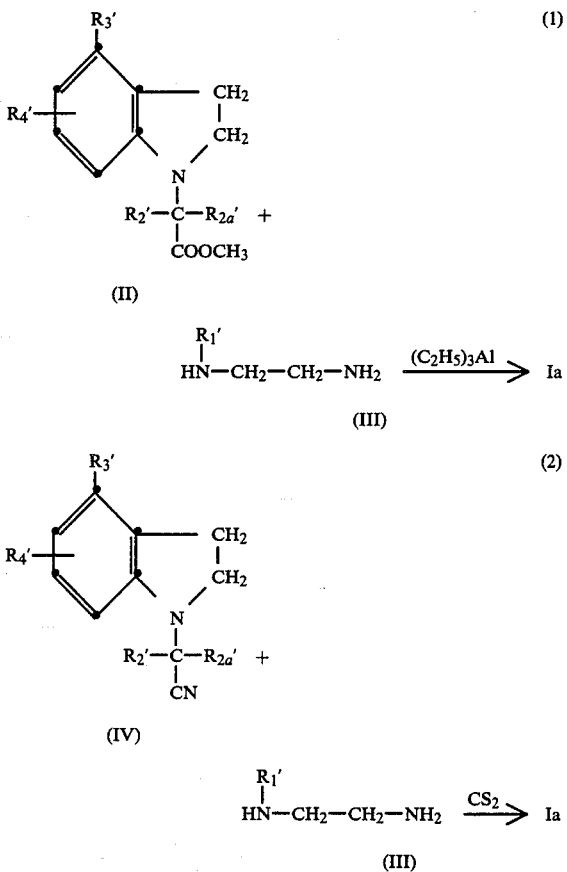

In the formulae II, III and IV, the symbols $R_1'$ to $R_4'$ have the meanings defined under the formula Ia.

The processes are performed under normal pressure, at a temperature of −25° to 150° C., preferably between 50° and 120° C., and if necessary in a solvent or diluent.

Suitable solvents or diluents are for example: ethers abd ethereal compounds, such as diethyl ether, diisopropyl ether, dioxane and tetrahydrofuran; aromatic hydrocarbons, such as benzene, toluene and xylenes; and halogenated hydrocarbons.

The starting materials of the formulae II, III and IV are known and can be produced by known methods.

The compounds of the formulae I and Ia are suitable for controlling pests on animals and plants.

The compounds of the formulae I and Ia are particularly suitable for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also mites and ticks of the order Acarina.

It is to be emphasised that the compounds according to the invention are characterised both by a strongly marked systemic as well as contact action against sucking insects, especially against sucking insects of the order Homoptera, and particularly against insects of the Aphididae family (for example *Aphis fabae, Aphis craccivora* and *Myzus persicae*), which can be controlled with known compositions only with great difficulty.

Besides having an action against mosquito larvae, compounds of the formulae I and Ia also have an action rendering them suitable for use in controlling insects that damage plants, especially insects that damage plants by eating, in crops of ornamental plants and productive plants, particularly in cotton and rice crops (for example against *Anthonomus grandis, Spodoptera littoralis, Heliothis virescens* and *Nilaparvata lugens*), as well as in fruit and vegetable crops (for example against *Laspeyresia pomonella, Leptinotarsa decemlineata* and *Epilachna varivestis*). The compounds of the formulae I and Ia are distinguished also by a good action against larval insect stages and nymphs; to be mentioned also is their broad ovicidal and ovilarvicidal action. When for example compounds of the formulae I and Ia are taken up with the feed by adult insect stages, there is observed in many cases, especially with Coleoptera, for example *Anthonomus grandis*, a reduced oviposition and/or a lessened rate of hatching. Furthermore, the compounds of the formulae I and Ia can be successfully used against plant-damaging cicadas, such as *Laodelphax striatellus*, as well as *Nilaparvata lugens*, and *Chilo suppressalis*, especially in rice crops.

The compounds of the formulae I and Ia can be used also for controlling ectoparasites, such as *Lucilia sericata*, and ticks, such as *Boophilus microplus*, on domestic animals and productive animals, for example by the treatment of animals, livestock housing and pasture land.

The action of the compounds of the formulae I and Ia and of the compositions containing them can be considerably broadened and adapted to suit prevailing conditions by the addition of other insecticides and/or acaricides. Suitable additives are for example the following active substances: organic phosphorus compounds, nitrophenols and derivatives thereof, formamidines, ureas, carbamates, chlorinated hydrocarbons and *Bacillus thuringiensis* preparations.

Compounds of the formulae I and Ia can be combined particularly advantageously also with substances having a pesticidally intensifying effect. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The good insecticidal action of the compounds of the formulae I and Ia corresponds to a mortality rate of at least 50-60% of the insect pests mentioned.

The compounds of the formulae I and Ia are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting scattering or pouring, and likewise the type of composition, are selected to suit the objectives to be achieved and the given conditions.

The formulations, that is to say, the compositions or preparations containing the active ingredients of the formulae I and Ia, or combinations of these active ingredients with other insecticides or acaricides, and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Depending on the nature of the active ingredients of the formulae I and Ia or of combinations of these active ingredients with other insecticides or acaricides, to be formulated, suitable surface-active compounds are: nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and in general contain an alkyl group having 8 to 22 C atoms, 'alkyl' including also the alkyl moiety of acyl groups, for example the Na or Ca salt of ligninsulfonic acid, of dodceylsulfuric acid ester or of a fatty alcohol sulfate mixture produced from natural fatty acids. Included amongst these are also the salts of sulfuric acid esters and of sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanomlamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the watersoluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1982; and Dr. Helmut Stache "Tenside Taschenbuch", Carl Hanser Verlag, Munich/Vienna, 1981.

The pesticidal preparations contain as a rule 0.1 to 99%, particularly 0.1 to 95%, of an active ingredient of the formula I or Ia, or of a combination of this active ingredient with other insecticides or acaricides, 1 to 99.9% of a solid or liquid additive, and 0 to 25% especially 0.1 to 20%, of a tenside.

Whereas commercial products are preferably in the form of concentrated compositions, the preparations employed by the end-user have as a rule a considerably lower concentration of active ingredient.

The compositions can also contain further additives, such as stabilisers, antifoaming agents, viscosity regulators, binders and adhesives, as well as fertilisers or other active ingredients for obtaining special effects.

FORMULATION EXAMPLES FOR LIQUID ACTIVE INGREDIENTS OF THE FORMULAE I AND Ia, OR FOR COMBINATIONS OF THESE ACTIVE INGREDIENTS WITH OTHER INSECTICIDES OR ACARICIDES
(%=PERCENT BY WEIGHT)

| 1. Emulsion concentrates | (a) | (b) | (c) |
|---|---|---|---|
| active ingredient or active-ingredient combination | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the required concentration can be produced from these concentrates by dilution with water.

| 2. Solutions | (a) | (b) | (c) | (d) |
|---|---|---|---|---|
| active ingredient or active-ingredient combination | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

These solutions are suitable for application in the form of very small drops.

| 3. Granulates | (a) | (b) |
|---|---|---|
| active ingredient or active-ingredient combination | 5% | 10% |
| kaolin | 94% | — |
| highly dispersed silicic acid | 1% | — |
| attapulgite | — | 90% |

The active ingredient or the active-ingredient combination is dissolved in methylene chloride, the solution is sprayed onto the carrier, and the solvent is then evaporated off in vacuo.

| 4. Dusts | (a) | (b) |
|---|---|---|
| active ingredient or active-ingredient combination | 2% | 5% |
| highly dispersed silicic acid | 1% | 5% |
| talcum | 97% | — |
| kaolin | — | 90% |

Dusts ready for use are obtained by the intimate mixing together of the carriers with the active ingredient or with the active-ingredient combination.

FORMULATION EXAMPLES FOR SOLID ACTIVE INGREDIENT OF THE FORMULAE I AND Ia, OR FOR COMBINATIONS OF THESE ACTIVE INGREDIENTS WITH OTHER INSECTICIDES OR ACARICIDES
(%=PERCENT BY WEIGHT)

| 5. Wettable powders | (a) | (b) | (c) |
|---|---|---|---|
| active ingredient or active-ingredient combination | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient or the active-ingredient combination is well mixed with the additives and the mixture is thoroughly ground in a suitable mill. Wettable powders which can be diluted with water to give suspensions of the required concentration are obtained.

| 6. Emulsion concentrate | |
|---|---|
| active ingredient or active-ingredient combination | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 7. Dusts | (a) | (b) |
|---|---|---|
| active ingredient or active-ingredient combination | 5% | 8% |
| talcum | 95% | — |
| kaolin | — | 92% |

Dusts ready for use are obtained by mixing the active ingredient or active-ingredient combination with the carriers, and grinding the mixture in a suitable mill.

| 8. Extruder granulate | |
|---|---|
| active ingredient or active-ingredient combination | 10% |
| sodium lignin sulfonate | 2% |
| carboxymethyl cellulose | 1% |
| kaolin | 87% |

The active ingredient or the active-ingredient combination is mixed and ground with the additives, and the mixture is moistened with water. This mixture is extruded, granulated, and then dried in a stream of air.

| 9. Coated granulate | |
|---|---|
| active ingredient or active-ingredient combination | 3% |
| polyethylene glycol (M.W. 200) | 3% |
| kaolin | 94% |

The finely ground active ingredient or active-gredient combination is evenly applied, in a mixer, to the kaolin moistened with polyethylene glycol. Dustfree coated granules are obtained in this manner.

| 10. Suspension concentrate | |
|---|---|
| active ingredient or active-ingredient combination | 40% |

| 10. Suspension concentrate | |
|---|---|
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient or the active-ingredient combination is intimately mixed with the additives. There is obtained a suspension concentrate from which can be produced, by dilution with water, suspensions of the concentration required.

EXAMPLE 1

Production of compound No. 1 of the formula

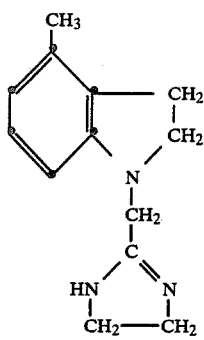

24.0 g of ethylenediamine are added dropwise at 5° C., under argon, to a two-molar solution of 45.7 g of $(C_2H_5)_3$ Al in abs. toluene. After the evolution of gas has finished, there are added dropwise 41.0 g of the compound of the formula

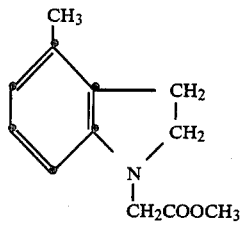

dissolved in 40 ml of toluene, and the mixture is stirred at 100° C. for 3 hours. A mixture of 85 ml of water, 280 ml of methanol and 280 ml of dichloromethane is subsequently carefully added dropwise at 30° C. under argon, and the reaction mixture is heated, with vigorous stirring, in 15 minutes to 90° C., and is then cooled to 20° C. and filtered. 1000 ml of ethyl acetate are added; the mixture is afterwards refluxed for 15 minutes on a steam bath, filtered, and concentrated in vacuo. Dry hydrogen bromide is introduced at 10° C. into the solution of the crude base in 400 ml of dichloromethane/carbon tetrachloride 1:4 until the solution is saturated. It is then concentrated by evaporation and recrystallised from water to yield the hydrobromide of the title compound having a melting point of 225°–226° C. In order to liberate the base, the salt is dissolved in a saturated bicarbonate solution, and extraction is carried out for 15 hours with dichloromethane. The organic phase is dried ($Na_2SO_4$), and concentrated in vacuo. The title product, m.p. 108°–110° C., is obtained after recrystallisation from ether/hexane 1:1.

The following compounds are obtained in an analogous manner.

| No. | $R_1$ | $R_2$ | $R_{2a}$ | $R_3$ | $R_4$ | [X] | Physical data |
|---|---|---|---|---|---|---|---|
| 2 | H | H | H | Cl | H | .HCl | m.p.: 225° C. dec. |
| 3 | H | H | H | Cl | H |  | m.p.: 110–112° C. |
| 4 | H | H | H | H | H |  | m.p.: 87–88° C. |
| 5 | H | H | H | $CH_3$ | H | .HBr | m.p.: 225–226° C. |
| 6 | H | H | H | H | H | .HBr | m.p.: 230° C. |
| 7 | H | H | H | H | 7-Cl | .HBr | m.p.: 250° C. |
| 8 | H | H | H | $CH_3$ | H | .HCl | m.p.: 200° C. |
| 9 | H | H | H | H | 7-$CH_3$ | .2HBr | m.p.: 172–175° C. |
| 10 | H | H | H | H | 7-Cl |  | m.p.: 100° C. |
| 11 | H | H | H | Cl | H | .HBr | m.p.: 181–185° C. |
| 12 | H | H | H | H | 7-$CH_3$ |  | m.p.: 100–102° C. |
| 13 | H | H | H | $CH_3$ | H | 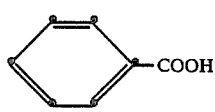 | m.p.: 145° C. |

-continued

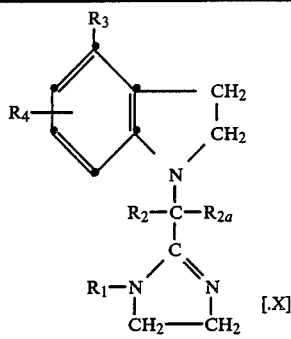

| No. | $R_1$ | $R_2$ | $R_{2a}$ | $R_3$ | $R_4$ | [.X] | Physical data |
|---|---|---|---|---|---|---|---|
| 14 | H | H | H | $CH_3$ | H | .$CF_3COOH$ | m.p.: 155° C. |
| 15 | H | H | H | $CH_3$ | H | .$CH_3$—⟨⟩—$SO_3H$ | m.p.: 160–161° C. |
| 16 | H | H | H | Cl | H | .$CH_3$—⟨⟩—$SO_3H$ | m.p.: 174–176° C. |
| 17 | H | H | H | Cl | H | .HOOC—COOH | m.p.: 224° C. |
| 18 | H | H | H | Cl | H | ⟨⟩—COOH | m.p.: 135–137° C. |
| 19 | H | H | H | Cl | H | .$CF_3COOH$ | m.p.: 147–149° C. |
| 20 | H | H | H | H | 5-Cl | | |
| 21 | H | H | H | $CH_3$ | 7-$CH_3$ | | |
| 22 | H | H | H | H | 6-$OCH_3$ | | |
| 23 | H | H | H | $CF_3$ | H | | |
| 24 | H | H | H | $OCH_3$ | H | | |
| 25 | H | H | H | F | H | | |
| 26 | H | H | H | Br | H | | |

(b) Production of the compound No. 27 of the formula

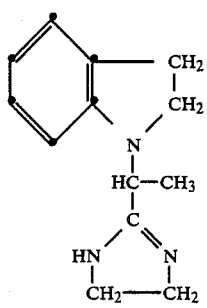

A solution of 0.02 mol of the compound of the formula

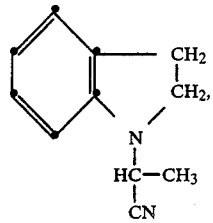

0.04 mol of ethylenediamine and 3–5 drops of carbon disulfide is vigorously stirred at a temperature of 110°–120° C. The reaction mixture is poured onto ice, and extracted with dichloromethane. The organic phase is washed three times with water and once with a saturated sodium chloride solution. After drying over sodium sulfate, concentration by evaporation and chromatography (silica gel; eluant: methyl alcohol/ammonia 20:1), there is obtained the title compound, which shows, in the mass spectrum, deflections at 215, 144, 130, 117 and 97 m/e.

The following compounds are produced in an analogous manner:

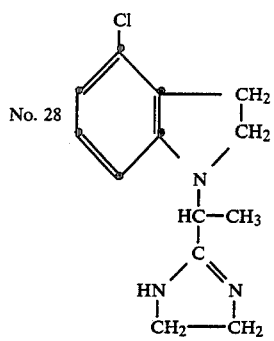 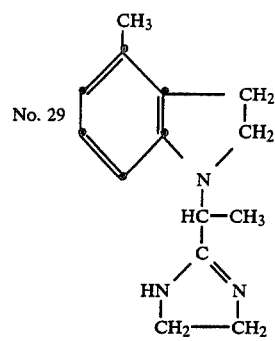

No. 28, No. 29

EXAMPLE 2

Insecticidal systemic action: *Aphis craccivora*

Rooted bean plants are transplanted to pots each containing 600 ccm of soil; and 50 ml of test solutions containing 25 ppm and 5 ppm, respectively, of the compound to be tested are subsequently poured directly onto the soil in each pot. After 24 hours, aphids (*Aphis craccivora*) are settled onto the parts of plants above the soil, and a plastics cylinder is placed over each plant and drawn to by tying at the bottom in order to protect the aphids from any contact or gas action of the test substance. An evaluation of the mortality rate achieved is made 48 hours after commencement of the test. Two plants, each in a separate pot, are used per concentration level of test substance. The test is carried out at 25° C. with 70% relative humidity.

The compounds according to Example 1 exhibit against *Aphis craccivora* the activity shown in the following Table.

Biological test results

In the following Table are summarised test results based on the Example given in the foregoing, the index of values with regard to the percentage mortality of the pests being as follows:

| Compound | Activity against *Aphis craccivora* |
|---|---|
| 1 | B |
| 2 | B |
| 3 | B |
| 4 | B |
| 5 | B |
| 6 | B |
| 7 | B |
| 8 | A |
| 9 | A |
| 10 | B |
| 11 | B |
| 12 | B |
| 13 | B |
| 14 | B |
| 15 | B |
| 16 | B |

A: 70–100% mortality with 5 ppm of active ingredient
B: 70–100% mortality with 25 ppm of active ingredient

EXAMPLE 3

Acaricidal action: *Boophilus microplus* (larvae)

For each concentration, 20 sensitive larvae and OP-resistant larvae, respectively (resistance is with respect to diazinon compatibility) are counted into a small glass tube, and immersed for 1 to 2 minutes in 2 ml of an aqueous emulsion from a dilution series of 100, 10, 1 or 0.1 ppm of test substance. The test tube in each case is then sealed with a standardised cotton plug and inverted so that the active-ingredient emulsion can be absorbed by the cotton wool.

The compounds according to Example 1 exhibit against *Boophilus microplus* the levels of activity shown in the following Table: Biological test results In the Table are summarised test results based on the Example given in the foregoing, the index of values with regard to the percentage mortality of the larvae of *Boophilus microplus* being as follows:

| | Activity against *Boophilus microplus* | |
|---|---|---|
| Compound No. | sensitive larvae | OP-resistant larvae |
| 1 | A | B |
| 2 | B | C |
| 3 | A | B |
| 4 | B | D |

A: 70–100% mortality with 0.1 ppm of active ingredient
B: 70–100% mortality with 1 ppm of active ingredient
C: 70–100% mortality with 10 ppm of active ingredient
D: 70–100% mortality with 100 ppm of active ingredient

EXAMPLE 4

Insecticidal stomach-poison action: *Nilaparvata lugens*

Rice plants are sprayed with a test solution containing 50 ppm of the compound to be tested. After the drying of the applied coating, larvae of *Nilaparvata lugens* ($L_3$ stage) are settled onto the plants. Two plants are used per test compound, and an evaluation of the mortality rate achieved is made after 24 hours. The test is carried out at 22° C. with 60% relative humidity.

Compounds according to Example 1 are 100% effective against *Nilaparvata lugens* larvae.

What is claimed is:

1. A compound of the formula

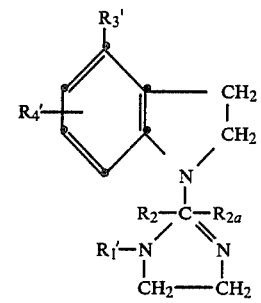

or a salt thereof, wherein $R_1$ is hydrogen or $C_1$–$C_{12}$-alkyl, $R_2$ and $R_{2a}$ independently of one another are each hydrogen or $C_1$–$C_4$-alkyl, or together are $C_2$–$C_4$-alkylene, $R_3$ and $R_4$ are independently hydrogen, halogen or $C_1$–$C_3$-alkoxy, or $C_1$–$C_4$-alkyl which is unsubstituted or substituted by halogen, provided that both $R_3$ and $R_4$ are not hydrogen.

2. A compound of claim 1, wherein
$R_1$ and $R_{2a}$ are hydrogen,
$R_2$ is hydrogen or $C_1$–$C_4$-alkyl,
$R_3$ is halogen or $C_1$–$C_3$-alkoxy, or $C_1$–$C_4$-alkyl which is unsubstituted or substituted by fluorine, and
$R_4$ is hydrogen, halogen or $C_1$–$C_4$-alkyl.

3. A compound of claim 2, wherein
$R_2$ and $R_4$ are hydrogen.

4. The compound of claim 3, of the formula

5. The compound of claim 3 of the formula

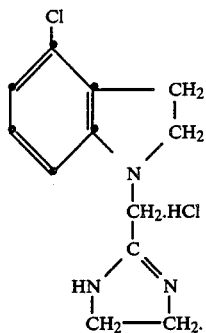

6. A composition for controlling insects and members of the order Acarina, which composition contains an effective amount of a compound of the formula

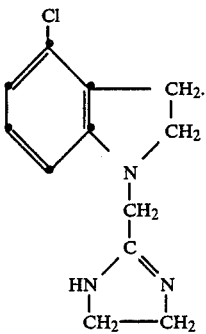

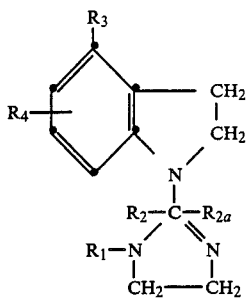

or a salt thereof, wherein
$R_1$ is hydrogen or $C_1$-$C_{12}$-alkyl,
$R_2$ and $R_{2a}$ independently of one another are each hydrogen or $C_1$-$C_4$-alkyl, or together are $C_2$-$C_4$-alkylene, and
$R_3$ and $R_4$ independently of one another are each hydrogen, halogen or $C_1$-$C_3$-alkoxy, $C_1$-$C_4$-alkyl which is unsubstituted or substituted by halogen, provided that both $R_3$ and $R_4$ are not hydrogen, together with a suitable carrier and/or other additive.

7. A composition of claim 6, wherein $R_1$ and $R_{2a}$ are hydrogen, $R_2$ is hydrogen, or $C_1$-$C_4$-alkyl, $R_3$ is halogen or $C_1$-$C_3$-alkoxy, or $C_1$-$C_4$-alkyl which is unsubstituted or substituted by fluorine, and $R_4$ is hydrogen, halogen or $C_1$-$C_4$-alkyl.

8. A composition of claim 7, wherein $R_2$ and $R_4$ are hydrogen.

9. A method of controlling insects and acarids on animals and plants, which method comprises applying thereto or to the locus thereof an effective amount of a composition containing a compound of the formula

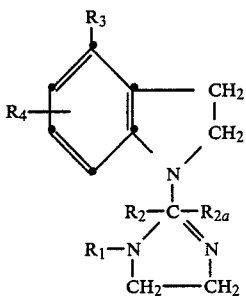

or a salt thereof, wherein
$R_1$ is hydrogen or $C_1$-$C_{12}$-alkyl,
$R_2$ and $R_{2a}$ independently of one another are each hydrogen or $C_1$-$C_4$-alkyl, or together are $C_2$-$C_4$-alkylene, and
$R_3$ and $R_4$ independently of one another are each hydrogen, halogen or $C_1$-$C_3$-alkoxy, or $C_1$-$C_4$-alkyl which is unsubstituted or substituted by halogen, together with a suitable carrier and/or other additive.

* * * * *